(12) United States Patent
Yamaguchi et al.

(10) Patent No.: US 7,530,692 B2
(45) Date of Patent: May 12, 2009

(54) OPHTHALMOLOGIC PHOTOGRAPHING APPARATUS

(75) Inventors: Tatsuo Yamaguchi, Tokyo (JP); Toshifumi Mihashi, Tokyo (JP)

(73) Assignee: Kabushiki Kaisha Topcon, Tokyo (JP)

( * ) Notice: Subject to any disclaimer, the term of this patent is extended or adjusted under 35 U.S.C. 154(b) by 15 days.

(21) Appl. No.: 11/812,092

(22) Filed: Jun. 14, 2007

(65) Prior Publication Data
US 2007/0291230 A1 Dec. 20, 2007

(30) Foreign Application Priority Data
Jun. 16, 2006 (JP) ............... 2006-167216

(51) Int. Cl.
*A61B 3/14* (2006.01)
*A61B 3/10* (2006.01)
(52) U.S. Cl. ..................... 351/206; 351/221
(58) Field of Classification Search ......... 351/205–206, 351/210, 221
See application file for complete search history.

(56) References Cited

U.S. PATENT DOCUMENTS

| 6,550,917 | B1 | 4/2003 | Neal et al. |
| 6,685,650 | B2 * | 2/2004 | Tanaka ............ 600/504 |
| 6,890,076 | B2 * | 5/2005 | Roorda ............ 351/205 |
| 7,270,415 | B2 | 9/2007 | Yamaguchi et al. |
| 2005/0219461 | A1 | 10/2005 | Hirohara |

FOREIGN PATENT DOCUMENTS

| JP | 2004-113405 A | 4/2004 |
| JP | 2004-159779 A | 6/2004 |
| JP | 2004-159784 A | 6/2004 |
| JP | 2004-329282 A | 11/2004 |
| JP | 2006-006362 A | 1/2006 |

OTHER PUBLICATIONS

U.S. Appl. No. 11/812,089, filed Jun. 14, 2007, Yamaguchi et al.
T. Yamaguchi, U.S. PTO Office Action, U.S. Appl. No. 11/812,089, filed May 9, 2008, 18 pages.
T. Yamaguchi, Notice of Allowance and Fee(s) Due, 11/812,089, Jan. 12, 2009, 7 pages.

* cited by examiner

*Primary Examiner*—Ricky L Mack
*Assistant Examiner*—Dawayne A Pinkney
(74) *Attorney, Agent, or Firm*—Foley & Lardner LLP

(57) ABSTRACT

Horizontal and vertical scanning mirrors for scanning over a large angle, and horizontal and vertical compact scanning mirrors for scanning over a small angle are disposed at pupil-conjugated positions. Light is emitted from a light source to a retina, and reflected light from a broad range of the retina is accumulated by a photodetector. The accumulated light is constructed as a low-magnification retinal image by an image constructing processor. A position for picking up a high-magnification image is indicated on the basis of the constructed low-magnification retinal image. The compact scanning mirrors are rotated so that a high-magnification retinal image is achieved at the indicated pickup position. The photodetector accumulates the reflection light from the retina, and constructs the high-magnification retinal image at the pickup position indicated by the image constructing processor.

20 Claims, 10 Drawing Sheets

RESULT EXAMPLE OF BLOOD FLOW RATE MEASURING MODE
$V_{ave} = 50.5 [m/s]$

LOW-MAGNIFICATION CONSTRUCTED RETINAL IMAGE

OPHTHALMOLOGIC PHOTOGRAPHING APPARATUS

BACKGROUND OF THE INVENTION

1. Field of the Invention

The present invention relates to an ophthalmologic photographing apparatus, and particularly to an ophthalmologic photographing apparatus having scanning mirrors of four or more systems.

2. Description of the Related Art

This application claims priority from Japanese Patent Application No. 2006-167216, filed Jun. 16, 2006, which is incorporated herein by reference in its entirety.

Only eyes include blood vessels which can be directly viewed without any surgical operations in a body. If a white blood cell can be observed in a blood flow, it helps to find general disorders such as diabetes. Since the size of a white blood cell is about 10 μm, however, it would be difficult for current retina cameras to measure it. It would be also very difficult to take moving images of a blood flow because the amount of light which can be allowed to be incident on an eye is restricted and the line of sight is not stable.

The following technologies have been disclosed by the assignee of present application. An eye-characteristic measurement apparatus which compensates for aberrations of an eye under measurement by a compensation optical section and measures precisely a minute aberration remaining after compensation is disclosed, for example, in Japanese Unexamined Patent Application Publication No. 2004-113405, No. 2004-159779, and No. 2004-159784. A retina observation apparatus which compensates a light beam reflected by an eye under measurement in order to improve retinal image quality and obtains an optimal image is disclosed, for example, in Japanese Unexamined Patent Application Publication No. 2004-329282. A retinal image observation apparatus which detects a displacement of an eye under measurement and moves a wavefront compensation device according to the detected shift position to compensate the wavefront is disclosed, for example, in Japanese Unexamined Patent Application Publication No. 2006-006362.

The conventional scanning type adaptive optics retina cameras have two scanning systems of horizontal and vertical directions (two systems). When the number of the scanning systems is set to three or more, the apparatus construction of the conventional scanning type adaptive optics retina camera is generally enormous in size. For example, when scanning systems are disposed at conjugated positions with a pupil, many positions conjugated with the pupil must be prepared.

SUMMARY OF THE INVENTION

The present invention has been implemented in view of the foregoing point, and has an object to provide an ophthalmologic photographing apparatus that can achieve a high-magnification retinal image at any position.

The present invention has another object to provide an adaptive optics retinal camera having scanning mirrors of four or more systems without making the apparatus enormous by disposing an MEMS (Micro Electro Mechanical Systems) scanning mirror in the neighborhood of a deformable mirror disposed at a pupil-conjugated position, for example.

Furthermore, the present invention has further object to provide an ophthalmologic photographing apparatus that can specify a rough position by a large-angle scanning mirror and observe a minute site in detail by a small-angle scanning mirror.

Still furthermore, the present invention has further object to provide an ophthalmologic photographing apparatus that can estimate a blood flow rate by scanning a part of a minute site at a high speed.

According to the present invention, scanning mirrors are provided to four systems, and horizontal and vertical mirrors for scanning over a large angle and horizontal and vertical mirrors for scanning over a small angle are prepared. A rough position can be specified by the large-angle scanning mirrors, and a minute site thereof can be observed in detail by the small-angle scanning mirrors. Furthermore, a part of the minute site can be linearly scanned at a high speed.

According to the solving means of this invention, there is provided an ophthalmologic photographing apparatus comprising:

a light source section for emitting illumination light to illuminate a retina of an eye under measurement;

an aberration measurement section for receiving a reflected light beam from the retina and measuring the aberrations of the eye under measurement;

an aberration compensation section having a wavefront compensation element for compensating for the reflected light beam from the retina on the basis of the aberrations measured by the aberration measuring section so as to offset the aberrations;

an illumination optical system that has a scanning mirror for scanning a part of the retina in a two-dimensional direction by the illumination light beam from the light source section and, illuminates the retina of the eye under measurement;

a light-receiving optical system for receiving the reflected light beam that is illuminated through a path including the scanning mirror, reflected from the retina and compensated in aberrations by the aberration compensation section;

a photodetector for receiving the light beam from the light-receiving optical system; and an image forming section for forming a retinal image according to a scan position of the scanning mirror and a light-reception signal of the photodetector, wherein the wavefront compensation element faces the scanning mirror, the scanning mirror and the wavefront compensation element are disposed at pupil-conjugated positions or at substantially pupil-conjugated positions.

According to the present invention, it can provide an ophthalmologic photographing apparatus that can achieve a high-magnification retinal image at any position.

According to the present invention, it can provide an adaptive optics retina camera having scanning mirrors of four or more systems without making the apparatus enormous by disposing an MEMS (Micro Electro Mechanical Systems) scanning mirror in the neighborhood of a deformable mirror disposed at a pupil-conjugated position, for example.

Furthermore, According to the present invention, it can provide an ophthalmologic photographing apparatus that can specify a rough position by a large-angle scanning mirror and observe a minute site in detail by a small-angle scanning mirror.

Still furthermore, According to the present invention, it can provide an ophthalmologic photographing apparatus that can estimate a blood flow rate by scanning a part of a minute site at a high speed.

DETAILED DESCRIPTION OF THE PREFERRED EMBODIMENT

A preferred embodiment according to the present invention will be described hereunder with reference to the accompanying drawings.

1. Outline

An embodiment of the present invention relates to an MEMS scanner confocal type adaptive optics retina camera that can achieve a high-magnification retinal image at any position. According to this embodiment, a retinal camera that can pick up an image with high magnification at any position can be provided by disposing two scanning mirrors adaptive to two directions of X and Y at positions near to a wavefront compensation element disposed at a pupil-conjugated position of a confocal adaptive optics retinal camera. A deformable mirror itself may be rotated in place of the scanning mirror.

Furthermore, scanning at an aimed position can be performed, the rate of blood flow can be roughly measured on the basis of a numerical variation of intensity by performing scanning one-dimensionally at a high speed.

2. Optical Arrangement

Figure 1:
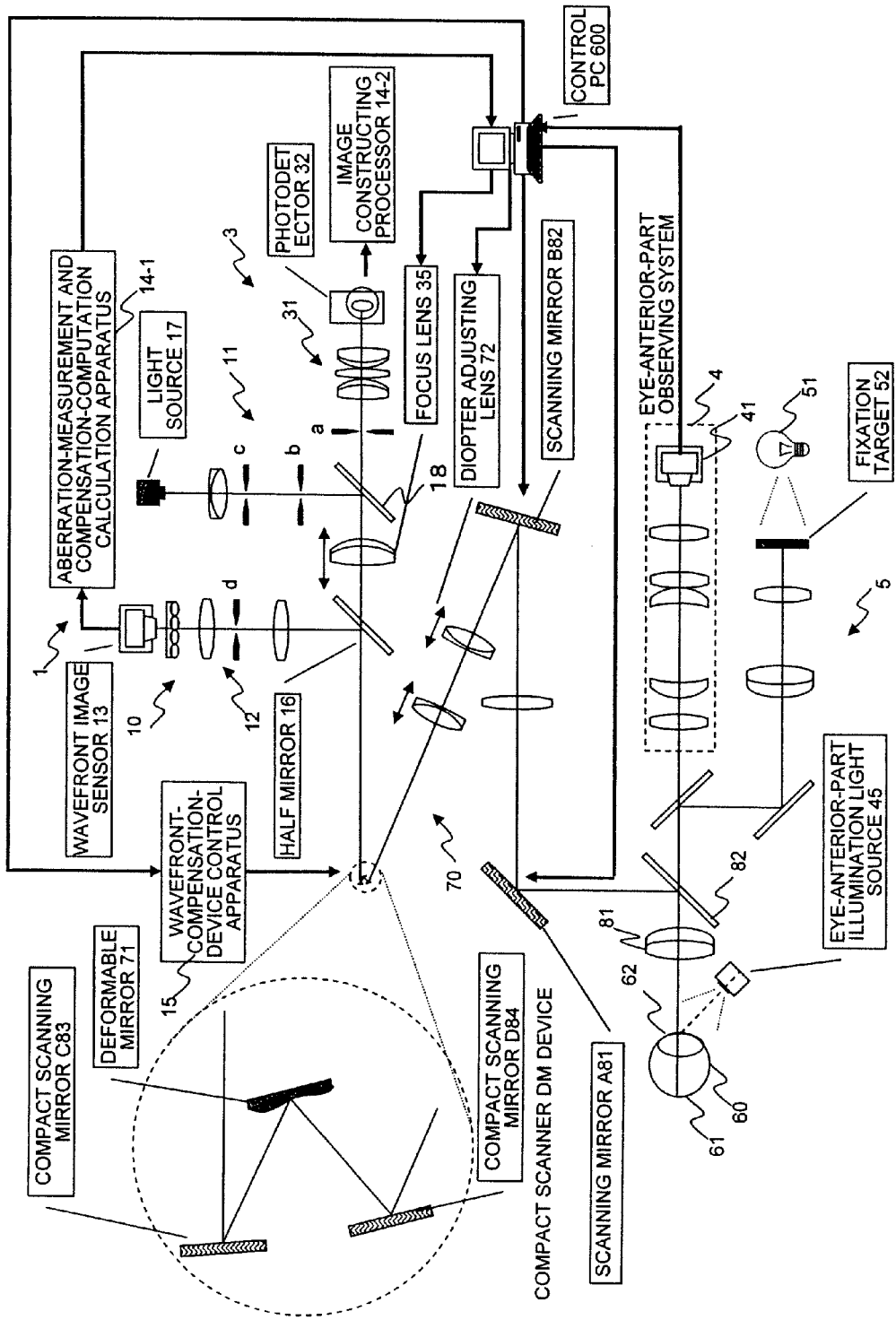
FIG. 1 is a diagram showing an optical arrangement of an embodiment of the present invention.

FIG. 1 is a diagram showing the optical arrangement of this embodiment.

A retina observing device (retina photographing device, adaptive optics retina camera) comprises a wavefront compensation system 1, a retina observing system 3, an eye-anterior-part observing system 4, an eye-anterior-part illumination light source 45, a fixation system 5, a compensation optical section 70 and a control PC (processor) 600.

The wavefront compensation system (aberration measuring section) 1 comprises a wavefront measuring system 10 having a first illumination optical system 11, a first light-receiving optical system 12 and a first light-receiving section 13, an aberration-measurement and compensation-computation calculation apparatus (aberration calculation section, hereinafter referred to as "calculation section") 14-1, and a wavefront-compensation-device control apparatus 15. The calculation section 14-1, an image constructing processor 14-2 and the control PC 600 may be equipped to one or plural processing sections. With respect to an eye 60 under measurement, an amphiblestrode (retina)61 and a cornea (eye anterior part) 62 are shown in FIG. 1.

The first illumination optical system 11 has a first light source section 17 and serves to illuminate a minute area (or target) on the retina of an eye under measurement by a light beam from the first light source section 17. Furthermore, the first illumination optical system 11 has plural scanning mirrors. The scanning mirror has a scanning mirror A81, a scanning mirror B82, a compact scanning mirror C83 and a compact scanning mirror D84, for example. The first illumination optical system 11 has aperture diaphragms c and d, and a beam splitter 18. The beam splitter 18 comprises a mirror (for example, polarized beam splitter) for reflecting a light beam from the first light source section 17 and transmitting therethrough a reflection light beam which is reflected from the amphiblestrode of the eye 60 under measurement and returned through an afocal lens 81.

SLD or a laser which is near to a point light source and has directivity is desirable as the first light source portion 17. In consideration of the load on a person being examined, it is better that the first wavelength of the first light source 17 for illumination is set to wavelengths in the range from the red light region to the near-infrared ray region (first wavelength). Furthermore, it is preferable that the spatial coherence is high, but the temporal coherence is not high. In this case, super luminescence diode (SLD) is adopted as the first light source section 17, and a point light source having high brightness can be achieved. The first light source section 17 is not limited to SLD, and a light source which is high both in spatial coherence and temporal coherence like a laser light source can be used although the image quality is slightly lowered. Even a light source which is not high both in spatial coherence and temporal coherence like LED could be used by inserting a pinhole or the like into the position of the light source in the optical path if it has a sufficient light amount.

The scanning mirrors A81 and B82 (second scanning mirrors) and the compact scanning mirrors C83 and D84 (scanning mirrors) are adaptable to the X and Y directions, so that a two-dimensional image can be achieved. For example, a broad range on the retina or the overall retina can be scanned by rotating the scanning mirrors A81, B82. The scanning mirrors A81, B82 can scan the retina with a rougher precision (first precision) than the compact scanning mirrors C83, D84. On the other hand, a narrow range on the retina or a part of the retina can be scanned by rotating the compact scanning mirrors C83, D84. For example, a desired position on the retina can be scanned. The compact scanning mirrors C83, D84 can scan the retina with a higher precision (second precision) than the scanning mirrors A81, B82, for example. With respect to the respective scanning mirrors, the image pickup position on the retina and the angle of the mirror are associated with each other in advance.

The scanning mirror A81 (first mirror) is disposed at a first position conjugated with a pupil, and the scanning mirror B82 (second mirror) is disposed at a second position which is different from the first position and conjugated with the pupil. The wavefront compensation element 71 is disposed at a third position conjugated with the pupil, and the compact scanning mirrors C83, D83 (third and fourth mirrors) are disposed in the vicinity of the third position and at positions which are substantially conjugated with the pupil. When the compact scanning mirrors C83 and D84 are excessively deviated from the pupil-conjugated position, there is a case where a desired light amount is not incident to a photodetector 32. Furthermore, in this embodiment, the mirror rotating in the X direction and the mirror rotating in the Y direction are used, however, one mirror which can rotate in both the X and Y directions may be used.

The first light-receiving optical system (point image light receiving optical system) 12 serves to receive a light beam reflected and returned from the amphiblestrode of the eye under measurement, and guide it to a first light receiving section (for example, a wavefront image sensor) 13. The first light receiving optical system 12 comprises an aperture diaphragm d, a relay lens, a half mirror 16, and a converting member (splitting element, for example, Haltman plate) for splitting a reflected light beam to at least seventeen beams. The converting member is a wavefront converting member for converting the reflected light beam to plural beams. Plural micro-Fresnel lenses disposed on a plane perpendicular to the optical axis may be used as the converting member. The reflection light from the retina 61 is condensed onto the first light receiving portion 13 through the converting member. The first light receiving section 13 receives light from the first light receiving optical system 12 which passes through the converting member, and generates a first signal.

The first illumination optical system 11 and the first light receiving optical system 12 keeps the relationship that a light beam from the first light source section 17 is assumed to be reflected at the condensed point thereof, the signal peak of the reflection light concerned at the first light receiving section 13 is maximum, and a diopter adjusting lens section 72 can be moved so that the signal peak at the first light receiving section 13 is intensified, and stopped at the position where the intensity of the signal peak is maximum. As a result, the light beam from the first light source section 17 is condensed on the eye under measurement.

The retina observing system 3 has a second light receiving optical system 31, a second light receiving section (for example, photodetector) 32, and an image constructing processor 14-2. The second light receiving optical system 31 comprises a focus lens 35, a afocal lens 81, a beam splitter 82 and a condenser lens. The second light receiving optical system 31 guides light reflected from the retina 61 through a compensation optical section 70 to the second light-receiving section 32. PD (PhotoDiode), a photomultiplier tube or the like may be used as the second light-receiving section 32. The second light-receiving section 32 receives light formed by the second light-receiving system 31, and generates a signal.

The focus lens 35 acts on both the optical systems of the light source 17 and the photodetector 32. For example, the focus lens 35 can change the depth position of the amphiblestrode. Specifically, amphiblestrode has a thickness of about 100 µm, and by moving the focus lens 35, it is determined which depth image along the thickness (about 100 µm) of the amphiblestrode is achieved.

In the foregoing description, for the sake of convenience, it is assumed that the afocal lens 81 and the beam splitter 82 are contained in the retina observing system 3 and the scanning mirrors and the beam splitter 18 are contained in the first illumination optical system 11. However, they may be contained in a proper system.

The compensation optical section (aberration compensation section) 70 has a wavefront compensation device 71 such as adaptive optical system (adaptive optics) for compensating measurement light for aberration, the moving prism (diopter-adjustment lens) 72 for moving along the optical axis to compensate a spherical component and/or a spherical lens. The compensation optical section 70 is disposed in the first and second light-receiving optical systems 12 and 31, and compensates, for example, for the aberration of a reflected light beam reflected by and returned from the eye under measurement 60. The compensation optical section 70 may compensate light emitted from the first light source 17 for aberration to illuminate a minute area on the retina of the eye under measurement by a light beam of which aberration has been compensated for.

The wavefront compensation device 71 can be a variable-shape mirror (a deformable mirror or a variable mirror) or a spatial light modulator such as liquid crystal. An appropriate optical system capable of compensating measurement light for aberration may also be used. A variable-shape mirror changes the reflection direction of light by deforming the mirror by an actuator provided inside the mirror. Other appropriate deforming methods can be used such as a deforming method using a capacitor or a piezoelectric device. A liquid-crystal spatial light modulator uses a liquid-crystal alignment characteristic to modulate a phase, and is used in reflection in many cases in the same way as the variable-shape mirror. When the liquid-crystal spatial light modulator is used, a polarizer is required in an optical path in some cases. The wavefront compensation device 71 may be a transmission-type optical system, in addition to a reflection-type optical system as example of FIG. 1. In this case, the compact scanning mirrors C83, D83 are disposed appropriately. The wavefront compensation device 71 compensates for aberration by, for example, being deformed according to the output of the wavefront-compensation-device control apparatus 15.

It is preferred that a parallel light beam be incident on the wavefront compensation device 71. Incident light is not limited to parallel light beams. When the eye under measurement 60 has no aberration, for example, light reflected from the retina of the eye under measurement 60 is incident on the wavefront compensation device 71 as a parallel light beam. Light emitted from the first light source section 17 is incident on the wavefront compensation device 71 as a parallel light beam.

The moving lens 72 is moved in the optical axis direction on the basis of the output from the control PC 600. For example, the moving lens 72 is driven by a proper driving section. The moving lens 72 is moved to compensate for the eye component. The eye component can be compensated by inserting an spherical lens, driving the internal optical system in the optical axis direction or the like in place of moving the moving lens 72.

There may be further provided a stage having a motor for calculating the moving amount of the pupil and moving the wavefront compensation element 71 in accordance with the output of a motor control circuit while following the calculated moving amount. For example, the wavefront compensation direction 71 is moved in a direction traversing the optical axis or on a plane vertical to the normal line. Accordingly, some point (for example, the center) of the wavefront compensation element 71 is conjugated with some point (for example, the pupil center) of the pupil at all times, and thus stable wavefront compensation can be performed.

The eye-anterior-part illumination light source 45 illuminates an eye anterior part of the eye under measurement 60. For example, a Placido's ring or a keratoring may be used to project a predetermined pattern on the eye anterior part. When a keratoring is used, a pattern just around the center of curvature of the cornea is obtained by a keratoimage. The wavelength of light emitted from the eye-anterior-part illumination light source 45 is, for example, different from the first wavelength, and can be a long wavelength (such as 940 nm).

The eye-anterior-part observation system 4 includes a condenser lens and an eye-anterior-part image sensor 41, and guides a light beam emitted from the eye-anterior-part illumination light source 45 and reflected by and returned from the cornea 62 of the eye under measurement 60, to the eye-anterior-part image sensor 41. As a light source section, an appropriate light source for illuminating the eye under measurement 60 may be used instead of the eye-anterior-part illumination light source 45. The eye-anterior-part observation system 4 can also guide a light beam reflected by and returned from the eye anterior part or the cornea 62 of the eye under measurement 60 when an appropriate pattern (such as a Placido's ring) is projected on the eye under measurement 60, to the eye-anterior-part image sensor 41. The eye-anterior-part image sensor 41 can obtain an eye-anterior-part image. The eye-anterior-part observation system 4 can also be used for alignment.

The third illumination optical system (fixation system) 5 includes, for example, an optical path for projecting an eyesight-target for making the eye under measurement 60 have fixation or clouding and fogging, and is provided with a third light source section (such as a lamp) 51, a fixation target 52, and a relay lens. The system 5 can project the fixation target 52 on the retina 61 with a light beam emitted from the third light source section 51, and makes the eye under measurement 60 observe its image.

The wavefront-compensation-device control apparatus 15 deforms the wavefront compensation device 71 according to the output of the control PC 600. For example, the wavefront-compensation-device control apparatus 15 generates a control signal (such as a voltage) for deforming each element of the wavefront compensation device 71, based on wavefront aberration measured by the calculation apparatus 14-1 or based on compensation obtained by the calculation apparatus 14-1, and outputs the generated control signal to the wavefront compensation device 71 to compensate the wavefront. The wavefront aberration and the amount of compensation can be calculated by the control PC 600.

The calculation apparatus 14-1 obtains optical characteristics that includes higher-order aberrations, of the eye under measurement 60 or of a light beam which was reflected by the eye under measurement 60 and of which aberrations have been compensated for by the compensation optical section 70, according to the output from the first light-receiving section 13. The calculation apparatus 14-1 may receive, instead of the output from the first light-receiving section 13, wavefront measurement data that indicates at least the wavefront aberration of the eye under measurement 60 to obtain the optical characteristics. The calculation apparatus 14-1 also determines the amount of compensation for the wavefront compensation device according to the obtained optical characteristics and outputs the amount of compensation to the wavefront-compensation-device control apparatus 15. The calculation apparatus 14-1 may output the amount of compensation etc. to the wavefront-compensation-device control apparatus 15 directly.

(Conjugate Relationship)

The retina 61 of the eye 60 under measurement, a fixation target 52 of the fixation system 5, the first light source section 17, the first light-receiving section 13, an aperture diaphragm a, an aperture diaphragm b, an aperture diaphragm d and the photodetector 32 are conjugated with one another. Furthermore, the pupil of the eye 60 under measurement (iris), the converting member (Haltman plate) of the first light-receiving optical system 12, an aperture diaphragm c, the wavefront compensation element (Deformable Mirror) 71 and the scanning mirrors A81 and B82 are conjugated with one another. The compact scanning mirrors C83 and D83 are substantially conjugated with the pupil.

(Alignment Adjustment)

Alignment adjustment will next be described. Alignment adjustment can be performed, for example, by the eye-anterior-part observation system 4.

Since an image of the eye under measurement 60 is formed on the eye-anterior-part image sensor 41 by the eye-anterior-part illumination light source 45 (light source section), which illuminates the cornea 62 of the eye under measurement 60, alignment adjustment needs to be performed such that the center of the pupil matches the optical axis by using the image of the eye under measurement 60.

When a light source for illuminating the eye under measurement 60 by parallel light beams through the condenser lens, the beam splitter 82, and the afocal lens 81 is added to the eye-anterior-part observation system 4, light beams reflected by the cornea 62 of the eye under measurement 60 are returned as if they were diverging from a point positioned at half the radius of curvature of the cornea 62. The diverging light beams pass through the afocal lens 81, the beam splitter 82, and the condenser lens, and the eye-anterior-part image sensor 41 receives the light beams as a spot image. If the spot image on the eye-anterior-part image sensor 41 is not on the optical axis, the retina observation apparatus is moved up and down and from side to side so that the spot image is on the optical axis. When the spot image is brought onto the optical axis, alignment adjustment is completed.

3. Electrical Construction

Figure 2:
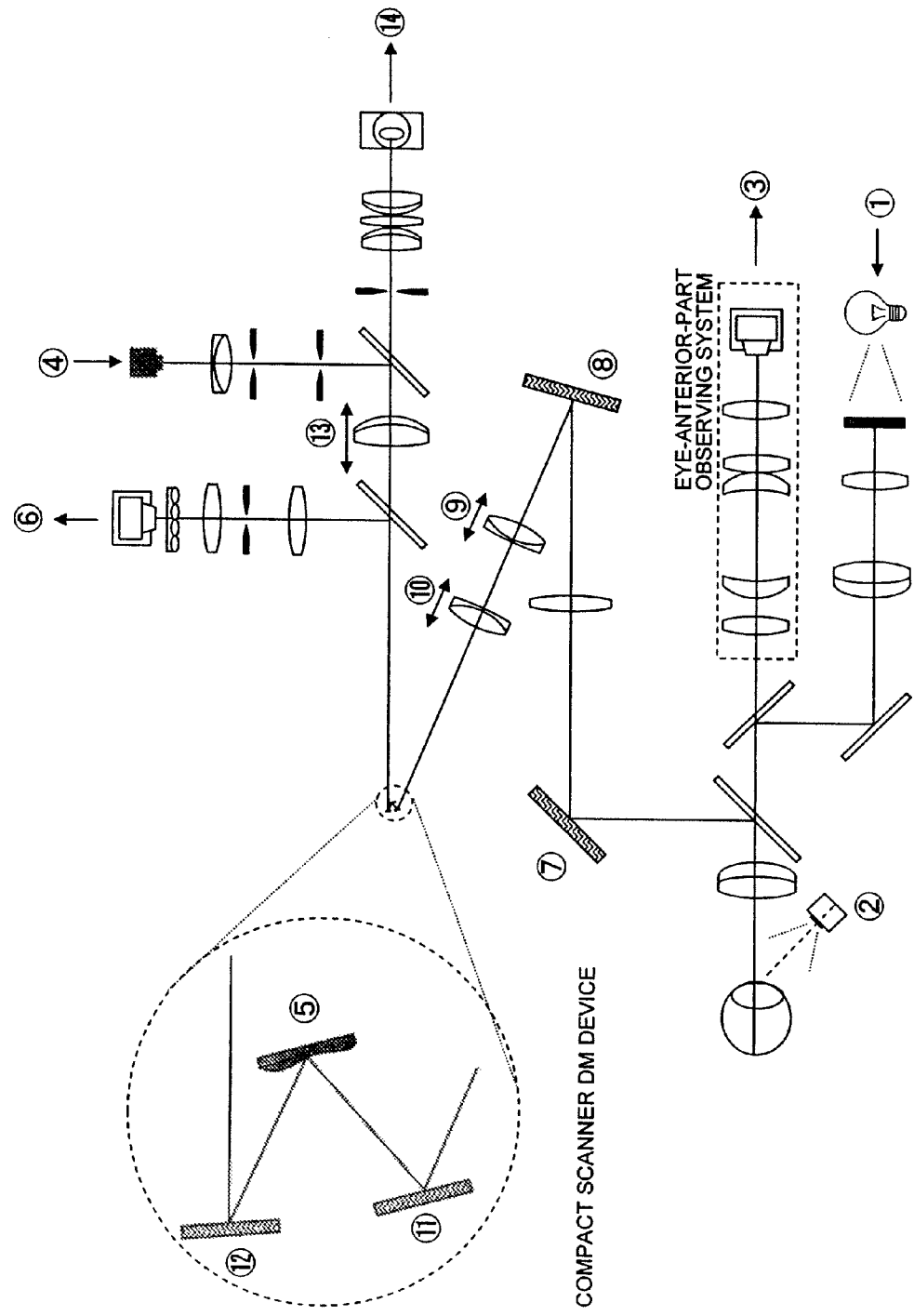
FIG. 2 is a diagram showing a signal in the embodiment.
Figure 3:
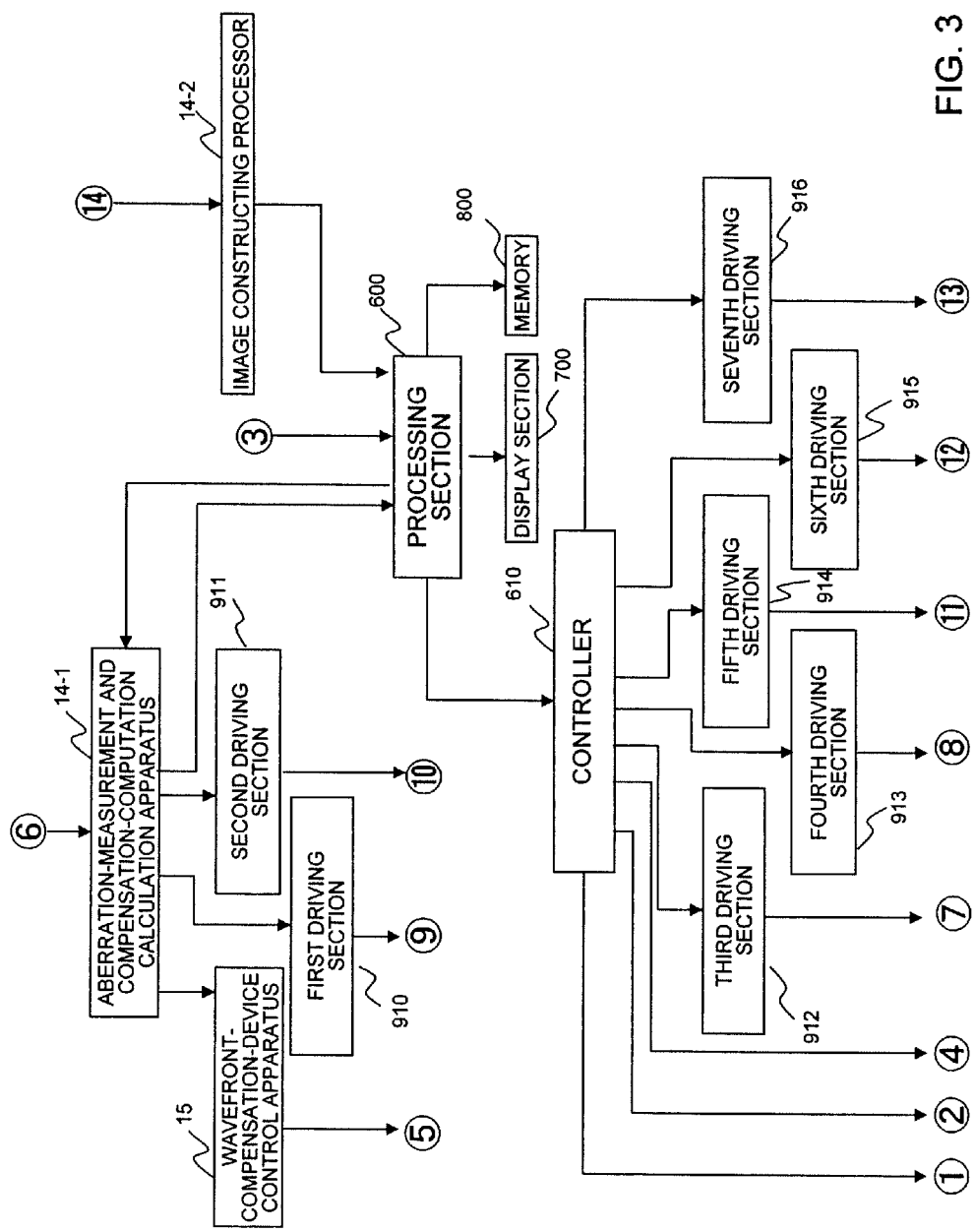
FIG. 3 is a block diagram showing an electrical system of this embodiment.

FIG. 3 is a block diagram showing the electrical system of this embodiment. FIG. 2 is a diagram showing a signal of this embodiment.

The electrical system of the ophthalmologic photographing apparatus includes a processor 600, a controller 610, a display section 700, a memory 800, a first driving section 910, a second driving section 911, a third driving section 912, a fourth driving section 913, a fifth driving section 914, a sixth driving section 915 and a seventh driving section 916. The ophthalmologic photographing apparatus may further comprise an input section. As the input section may be provided a pointing device for indicating proper buttons, icons, positions, areas, etc. displayed on the display section 700, a keyboard for inputting various kinds of data, etc.

The processor 600 is supplied with a signal (3) from the eye-anterior-part observing system 4, a signal from the calculation section 14-1 and a signal from the image constructing processor 14-2. The processor 600 is supplied with the signal (3) from the eye-anterior-part observing system 4 to adjust alignment, etc., for example. The processor 600 properly outputs the signals corresponding to these processing or other signals/data to the controller 610 for controlling the electrically driving system, the display section 700, the memory 800 and the calculation section 14-1.

The controller 610 controls turn-on or turn-off of the first light source section 17, the third light source section 51 and the eye-anterior-part illumination light source 45 and controls the third driving section 912 to the seventh driving section 916, etc. on the basis of the control signals from the processor 600. The controller 610 outputs the signal (1) to the third light source section 51, outputs the signal (2) to the eye-anterior-part illumination light source 45, outputs the signal (4) to the first light source section 17 and further outputs the signals to the third driving section 912 to the seventh driving section 916 on the basis of the signals corresponding to the operation result of the processor 600.

The first signal (6) from the first light-receiving section 13 is input to the calculation section 14-1 for calculating the compensation amount for aberration amount measurement. The calculation section 14-1 calculates the aberration of the eye 60 under measurement, the optical characteristics such as aberration amount, etc., the compensation amount for compensation of the wavefront compensation element 71, etc. on the basis of the input signal. The calculation section 14-1 properly outputs the signals corresponding to the operation result or other signals/data to the processor 600, the wavefront-compensation-device control apparatus 15, the first driving section 910 and the second driving section 911. The processor 14-1 may contain the processor 600. Furthermore, the first driving section 910 and the second driving section 911 may receive signals through the controller 610.

The image constructing processor (image forming section) 14-2 receives a signal (14) from the second light-receiving section 32. The image constructing processor 14-2 constructs a retinal image, etc. on the basis of the scan position and the input signal, and outputs the signal corresponding to the constructed retinal image or the like or other signals/data to the processor 600, for example.

The wavefront-compensation-device control apparatus 15 outputs a signal (5) on the basis of the signal input from the calculation section 14-1 to control the wavefront compensation element 71 so that aberration is compensated. The display section 700 displays an image pickup result (retinal image or the like). The memory 800 properly stores the measured aberration, the accumulation amount of take-in light, the constructed image, the time, etc. as occasion demands. The processor 600 properly reads out data from the memory 800 and writes data into the memory 800.

The first driving section 910 and the second driving section 911 output signals (9) and (10) respectively to move the moving means of the moving lenses 72, whereby the moving lenses 72 are moved in the optical axis direction. The third driving section 912 outputs a signal (7) to rotate the scanning mirror A81, for example. The fourth driving section 913 outputs a signal (8) to rotate the scanning mirror B82, for example. The fifth driving section 914 outputs a signal (11) to rotate the compact scanning mirror C83, for example. The sixth driving section 915 outputs a signal (12) to rotate the compact scanning mirror D84, for example. The seventh driving section 916 outputs a signal (13) to move the focus lens 35 in the optical axis direction, for example, and drives the moving means of the focus lens 35.

4. Aberration Measurement

Next, an aberration measurement (a Zernike analysis) will be described. A generally known method of calculating Zernike coefficients $C_i^{2j-i}$ from Zernike polynomials will be described. The Zernike coefficients $C_i^{2j-i}$ are important parameters for grasping the optical characteristic of the subject eye 60 on the basis of inclination angles of the light fluxes obtained by the first light receiving part 13 through the conversion member, for example Hartmann plate.

Wavefront aberrations W(X, Y) of the subject eye 60 are expressed using the Zernike coefficients $C_i^{2j-i}$ and the Zernike polynomials $Z_i^{2j-i}$ by the following expression.

$$W(X, Y) = \sum_{i=0}^{n} \sum_{j=0}^{i} c_i^{2j-i} Z_i^{2j-i}(X, Y)$$

Where, (X, Y) denotes vertical and horizontal coordinates of the Hartmann plate.

Besides, with respect to the wavefront aberrations W(X, Y), when the horizontal and vertical coordinates of the first light receiving part 13 are denoted by (x, y), a distance between the Hartmann plate and the first light receiving part 13 is denoted by f, and a movement distance of a point image received by the first light receiving part 13 is denoted by (Δx, Δy), the following expression is established.

$$\frac{\partial W(X, Y)}{\partial X} = \frac{\Delta x}{f}$$

-continued
$$\frac{\partial W(X, Y)}{\partial Y} = \frac{\Delta y}{f}$$

Where, the Zernike polynomials $Z_i^{2j-i}$ are expressed by the following numerical expressions. (More specifically expressions, for example, see JP-A-2002-209854.)

$$Z_n^m = R_n^m(r) \left\{ \begin{matrix} \sin \\ \cos \end{matrix} \right\} \{m\theta\}$$

$m > 0$ sin $m \leq 0$ cos $$R_n^m(r) = \sum_{S=0}^{(n-m)/2} (-1)^S \frac{(n-S)!}{S! \left\{ \frac{1}{2}(n-m) - S \right\}! \left\{ \frac{1}{2}(n+m) - S \right\}!} r^m$$

Incidentally, with respect to the Zernike coefficients $C_i^{2j-i}$, specific values can be obtained by minimizing the squared error expressed by the following numerical expression.

$$S(x) = \sum_{i=1}^{data\ number} \left[ \left\{ \frac{\partial W(X_i, Y_i)}{\partial X} - \frac{\Delta x_i}{f} \right\}^2 + \left\{ \frac{\partial W(X_i, Y_i)}{\partial Y} - \frac{\Delta y_i}{f} \right\}^2 \right]$$

Where, W(X, Y): wavefront aberrations, (X, Y): Hartmann plate coordinates, (Δx, Δy): a movement distance of a point image received by the first light receiving part 13, f: a distance between the Hartmann plate and the first light receiving part 13.

The calculation apparatus 14-1 calculates the Zernike coefficients $C_i^{2j-i}$, and uses this to obtain eye optical characteristics such as spherical aberrations, coma aberrations, and astigmatism aberrations. The calculation apparatus 14-1 calculates aberration quantities $RMS_i^{2j-i}$ using the Zernike coefficients $C_i^{2j-i}$ by the following numerical expression.

$$RMS_i^{2j-i} = \sqrt{\frac{\varepsilon_i^{2j-i}}{2(i+1)}} \, c_i^{2j-i}$$

$$\left( \varepsilon_i^{2j-i} = 2(2j = i), \varepsilon_i^{2j-i} = 1(2j \neq i) \right)$$

5. Operation

Figure 4:
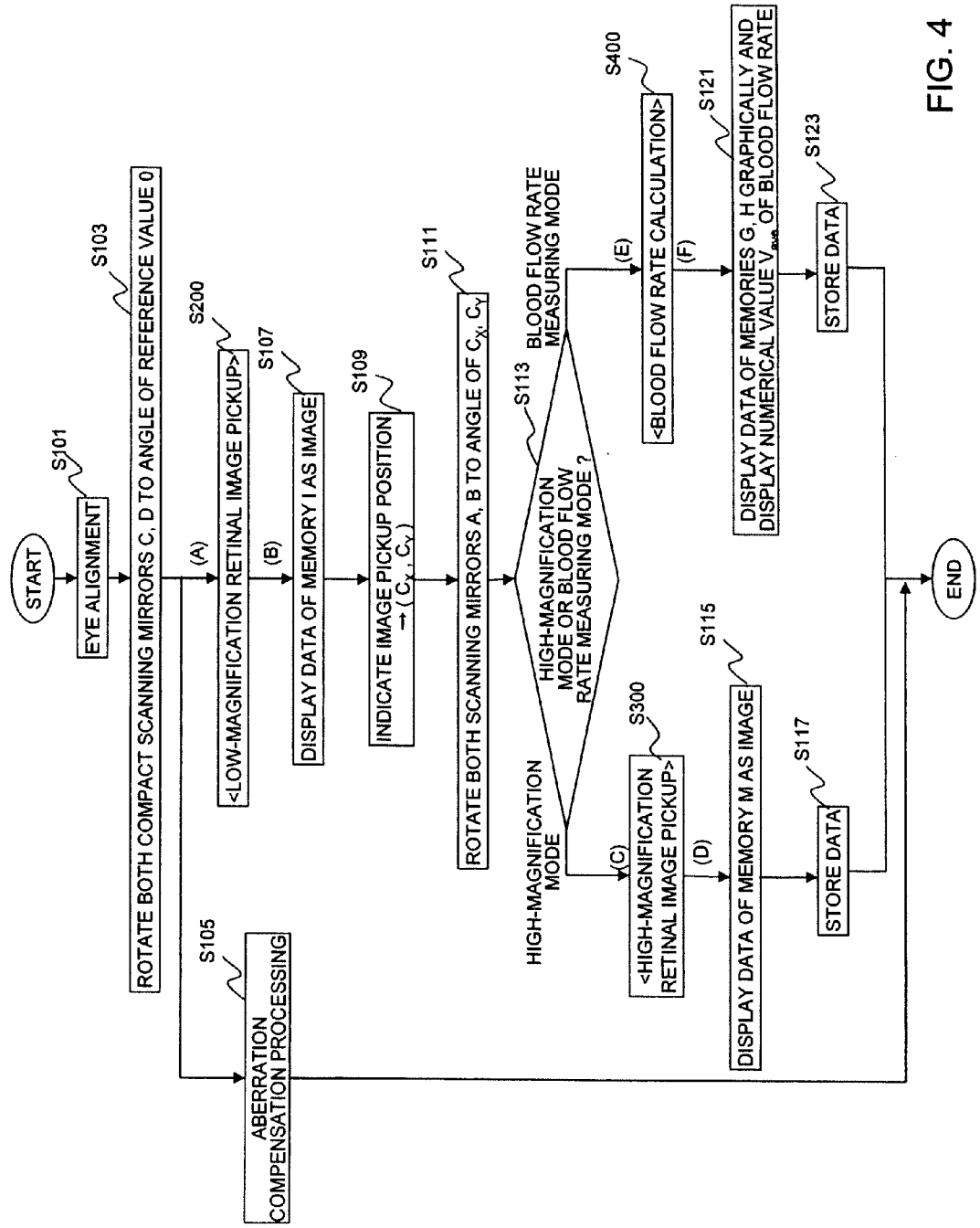
FIG. 4 is an overall flowchart of this embodiment.

FIG. 4 is the overall flowchart of this embodiment.

First, the processor 600 carries out eye alignment (S101). A spot for alignment may be used as another light source for eye alignment. In this embodiment, for example, a reflected light beam of a light beam projected to the eye anterior part is incident to the eye-anterior-part image sensor 41, and the whole apparatus or the eye is moved by an operator so that the center of the eye anterior part is coincident with the original point of the eye-anterior-part image sensor 41, whereby the eye alignment can be performed. The eye alignment may be carried out at a proper timing.

The processor 600 rotates both the compact scanning mirrors C83 and D84 to be the angle corresponding to a reference value 0 (S103). For example, the processor 600 controls the fifth driving section 914 and the sixth driving section 915 by the controller 610 to set the compact scanning mirrors C83 and D84 to the angle corresponding to the predetermined reference value 0.

The processor 600 executes aberration compensation processing (S105). The aberration compensation processing will be described hereunder. The aberration compensation processing may be executed prior to the processing subsequent to step S200 described later, or executed in parallel to or in the progress of the processing concerned.

For example, the calculation section 14-1 reads an image from the wavefront image sensor 13 and calculates the wavefront aberration on the basis of the read image. Furthermore, the calculation section 14-1 calculates the aberration amount R of the eye on the basis of the measurement result of the aberration measurement (for example, Zernike coefficients of $c_i^{2j-i}$), and stores the calculation result into the memory 800. The aberration amount R may be calculated as the standard deviation between the measurement result and the ideal wavefront (non-aberration). However, it can be easily calculated according to the following equation by using the Zernike coefficients. "order" in the equation represents the order of the Zernike coefficients, and for example, it is set like order=4, order=6 or the like.

$$R = \sqrt{\sum_{i=0}^{order}\sum_{j=0}^{i}\frac{\varepsilon_i^{2j-i}}{2(i+1)}(c_i^{2j-i})^2}$$

$$(\varepsilon_i^{2j-i} = 2(2j=i), \varepsilon_i^{2j-i} = 1(2j \neq i))$$

For example, when the calculated aberration amount R is not less than a predetermined threshold value, the calculation section 14-1 moves the moving lenses 72 through the first driving section 910 and the second driving section 911, and controls the wavefront compensation element 71 through the wavefront-compensation-device control apparatus 15, thereby compensating the aberration so as to offset the measured aberration.

In step S200, the processor 600 picks up a low-magnification retinal image of the eye 60 under measurement (S200). For example, the processor 600 rotates the scanning mirrors A81 and B82 to scan the retina, and the light accumulation amount at the photodetector 32 is stored in association with each scan position in the memory 800 (in this case, memory I). The detailed processing of picking up the low-magnification retinal image will be described later. The processor 600 reads out data in the memory I and displays the read-out data as an image on the display section (S107).

The processor 600 indicates a pickup position ($C_X$, $C_Y$) (S109). A desired position or range may be input through the input section by operator's manipulation to indicate the pickup position. For example, one point or area on an image may be clicked according to the low-magnification retinal image displayed on the display section 700 through the input section. The processor 600 may automatically indicate the pickup position.

The processor 600 rotates the scanning mirrors A81 and B82 to be the angles corresponding to the indicated pickup position ($C_X$, $C_Y$) respectively (S111). Subsequently, the processor 600 judges whether the mode is a high-magnification mode or a blood flow rate measuring mode (S113). For example, the processor 600 may display an indication for promoting specification of the mode on the display section 700 so that the operator makes an input from the input section, or a mode for measurement may be preset. Both the high-magnification mode and the blood flow rate measuring mode may be provided, or any one of them may be provided.

When the high-magnification mode is indicated (S113), the processor 600 picks up a high-magnification retinal image of the eye 60 under measurement (S300). For example, the processor 600 rotates the compact scanning mirrors C83 and D84 to scan the periphery of the pickup position ($C_X$, $C_Y$), and stores the light accumulation amount in the photodetector 32 in association with each scan position into the memory 800 (in this case, a memory M). The detailed processing of picking up the high-magnification retinal image will be described later. The processor 600 reads out data of the memory M, and displays the data as an image on the display section 700 (S115). The processor 600 stores proper data into the memory 800 (S117). The step S117 may be omitted.

When the blood flow rate measuring mode is indicated in step S113 (S113), the processor 600 calculates the blood flow rate (S400). For example, the processor 600 rotates the compact scanning mirrors C83 and D84 to scan the retina along a circle containing the pickup position ($C_X$, $C_Y$) at the center thereof (or a proper rotational orbit), for example, and calculates the rate Vave of a moving member such as blood stream or the like on the basis of the light accumulation amount in the photodetector 32. The detailed calculation of the blood flow rate will be described later.

The processor 600 read out data from the memory 800 (in this case, it is assumed to be memories G and H) ion which the light accumulation amount of the photodetector 32 is stored through the blood flow rate calculation, and displays the read-out data, for example as a graph, on the display section 700 (S121). The processor 600 displays the numerical value Vave of the calculated blood flow rate on the display section 700 (S121). The processor 600 stores proper data into the memory 800 (S123). The step S123 may be omitted.

(Low-Magnification Mode)

Figure 5:
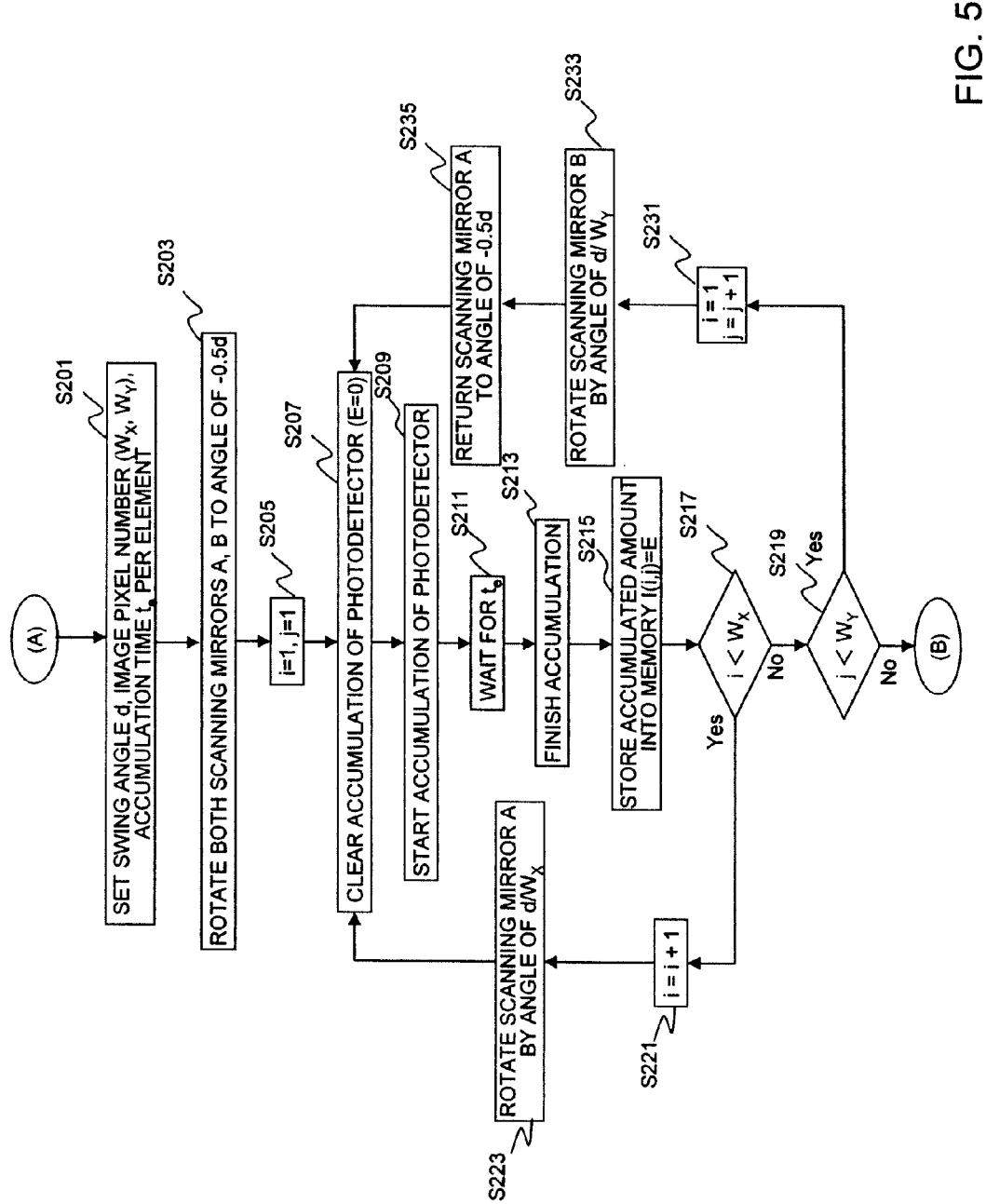
FIG. 5 is a flowchart showing low-magnification retinal image pickup.

FIG. 5 is a flowchart of low-magnification retinal image pickup, and a detailed flowchart of the step S200.

The processor 600 sets the swing angle d of the scanning mirrors A81 and B82, the number of image pixels ($W_X$, $W_Y$) and the accumulation time te per element (S201). The swing angle d, the image pixel number ($W_X$, $W_Y$) and the accumulation time te per element may be input by a proper input device or the like, or values stored in the memory 800 in advance may be read out. With respect to the swing angle d, the swing angle of the scanning mirror A81 and the swing angle of the scanning mirror B82 may be independently set.

The processor 600 rotates both the scanning mirrors A81 and B82 according to the set swing angle d to be the angle −0.5 d (S203). For example, the processor 600 controls the third driving section 912 and the fourth driving section 913 by the controller 610, and rotates the scanning mirror A81 and the scanning mirror B82.

The processor 600 initializes the parameters (S205). For example, the processor 600 sets the parameters i and j so that i=1 and j=1. Here, i represents the number of photodetections in the X-axis direction, and j represents the number of photodetections in the Y-axial direction. The processor 600 clears the accumulation of light of the photodetector 32 (the accumulation amount E=0) (S207).

The processor 600 starts illumination from the light source 17 at a proper timing, and starts light accumulation of the photodetector 32 (S209). The processor 600 waits for the set accumulation time te per element (S211). After the time te second elapses, the processor 600 finishes the light accumulation of the photodetector 32 (S213). The processor 600 stores the amount E accumulated by the photodetector 32 into the memory 800 (S215). For example, the processor 600 stores the amount E accumulated in the photodetector 32 into the memory 800 in association with the image pixel (i, j) (I(I, j)).

The processor 600 judges whether the parameter i is smaller than the pixel number $W_X$ (i<$W_X$) (S217). That is, it is judged whether the pixel number $W_X$ in the X-direction of the preset image pixel number ($W_X$, $W_Y$) is detected.

When the parameter i is smaller than $w_X$ (S217), the processor 600 increments the value of i (for example, i=i+1) (S221). The processor 600 rotates the scanning mirror A81 by the angle of d/$W_X$ (S223), and then returns to the step S207. For example, the processor 600 controls the third driving section 912 by the controller 610 to rotate the scanning mirror A81 by the angle of d/$W_X$ (scan in the X-axial direction).

On the other hand, when the parameter i is not smaller than $W_X$ (S217), the processor 600 judges whether the parameter j is smaller than $W_Y$ (j<$W_Y$). That is, it judges whether the pixel number $W_Y$ in the Y-direction of the preset image pixel number ($W_X$, $W_Y$) is detected.

When the parameter j is smaller than $W_Y$ (S219), the processor 600 returns the value of i to the initial state (for example, i=1), and also increments the value of j (for example, j=j+1) (S231). The processor 600 rotates the scanning mirror B82 by the angle of d/$W_Y$ (S233). Furthermore, the processor 600 returns the scanning mirror A81 to the angle of −0.5 d (S235), and then returns to the step S207. In this flowchart, the angle of the scanning mirror A81 is returned and scanned in the minus direction. However, it may scan in the opposite direction without returning the angle. At this time, in step S215, the parameters i, j are corrected so as to correspond to the position on the image and then stored.

As described above, the processor 600 repetitively executes the processing of the steps S207 to S219. When light of the set image pixel number ($W_X$, $W_Y$) is detected, the processing of picking up the low-magnification retinal image is finished (B).

(High-Magnification Mode)

Figure 6:
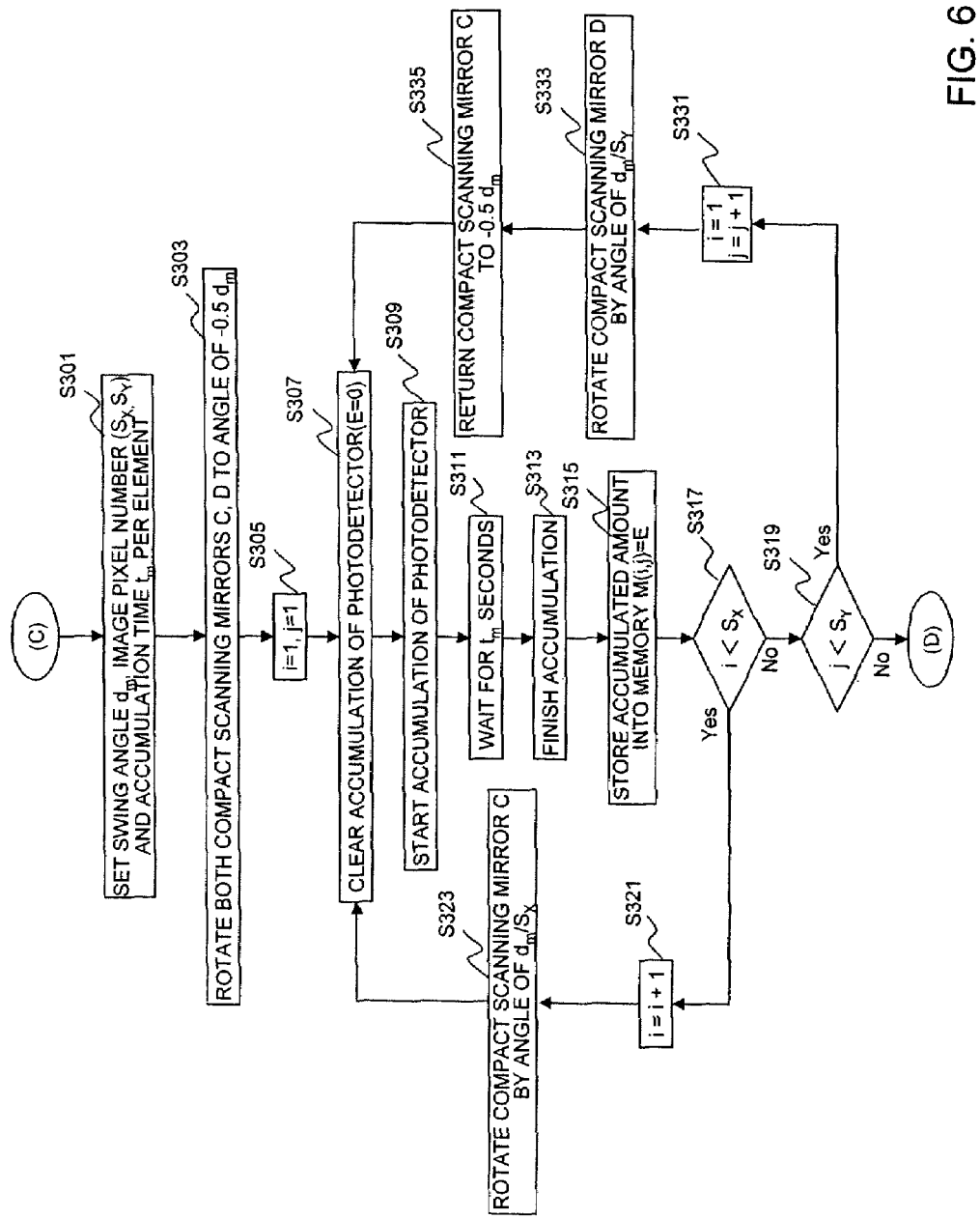
FIG. 6 is a flowchart showing high-magnification retinal image pickup.

FIG. 6 is a flowchart of picking up a high-magnification retinal image, and a detailed flowchart of the above step S300.

The processor 600 sets the swing angle dm of the compact scanning mirrors C83 and D84, the number of image pixels ($S_X$, $S_Y$) and the accumulation time tm per element (S301). The swing angle dm, the image pixel number ($S_X$, $S_Y$) and the accumulation time tm per element may be properly input by an input device or the like, or values stored in the memory 800 in advance may be read out. When an image pickup area is indicated in step S109, the swing angle dm may be set so that the area concerned can be scanned. In the swing angle dm, the swing angle of the compact scanning mirror C83 and the swing angle of the compact scanning mirror D84 may be independently set.

According to the set swing angle dm, the processor 600 rotates both the compact scanning mirrors C83 and D84 to be the angle −0.5 dm (S303). For example, the processor 600 controls the fifth driving section 914 and the sixth driving unit 915 by the controller 610 to rotate the compact scanning mirror C83 and the scanning mirror D84.

The processor 600 initializes the parameters (S305). For example, the processor 600 sets the parameters i and j so that i=1 and j=1. In this case, i represents the number of photodetections in the X-axial direction, and j represents the number of photodetections in the Y-axial direction, for example. The processor 600 clears the accumulation of light of the photodetector 32 (accumulation amount E=0) (S307).

The processor 600 starts the light accumulation of the photodetector 32 (S309). The processor 600 waits for the set accumulation time tm per element (S311). After tm second elapses, the processor 600 finishes the light accumulation of the photodetector 32 (S313). The processor 600 stores the amount E accumulated by the photodetector 32 into the memory 800 (S315). For example, the processor 600 stores the amount E accumulated in the photodetector 32 in association with the image pixel (i, j) into the memory 800 (M(i, j)).

The processor 600 judges whether the parameter i is smaller than the set number of pixels $S_X$ (i<$S_X$) (S317). That is, the processor 600 judges whether the pixel number $S_X$ in the X direction of the preset image pixel number ($S_X$, $S_Y$) is detected or not.

When the parameter i is smaller than $S_X$ (S317), the processor 600 increments the value of i (for example, i=i+1) (S321). The processor 600 rotates the compact scanning mirror C83 by the angle of dm/$S_X$ (S323), and then returns to the step S307. For example, the processor 600 controls the fifth driving unit 914 by the controller 610 to rotate the scanning mirror C83 by the angle of dm/$S_X$ (scan in the X-axial direction).

On the other hand, when the parameter i is not smaller than $S_X$ (S317), the processor 600 judges whether the parameter j is smaller than $S_Y$ (j<$S_Y$). That is, it judges whether the pixel number $S_Y$ in the Y-direction of the preset image pixel number ($S_X$, $S_Y$) is detected or not.

When the parameter j is smaller than $S_Y$ (S319), the processor 600 returns the value of i to the initial state (for example, i=1), and also increments the value of j (for example, j=j+1) (S331). The processor 600 rotates the compact scanning mirror D84 by the angle of dm/$S_Y$ (S333). Furthermore, the processor 600 returns the compact scanning mirror C83 to the angle of −0.5 dm (S335), and then returns to the step S307. The compact scanning mirror C83 may scans in the opposite direction without returning the angle as in the case of the above-described flowchart.

As described above, the processor 600 repeats the processing of the steps S307 to S319. when light of the set image pixel number ($S_X$, $S_Y$) is detected, the processing of picking up the high-magnification retinal image is finished (D).

Figure 9:
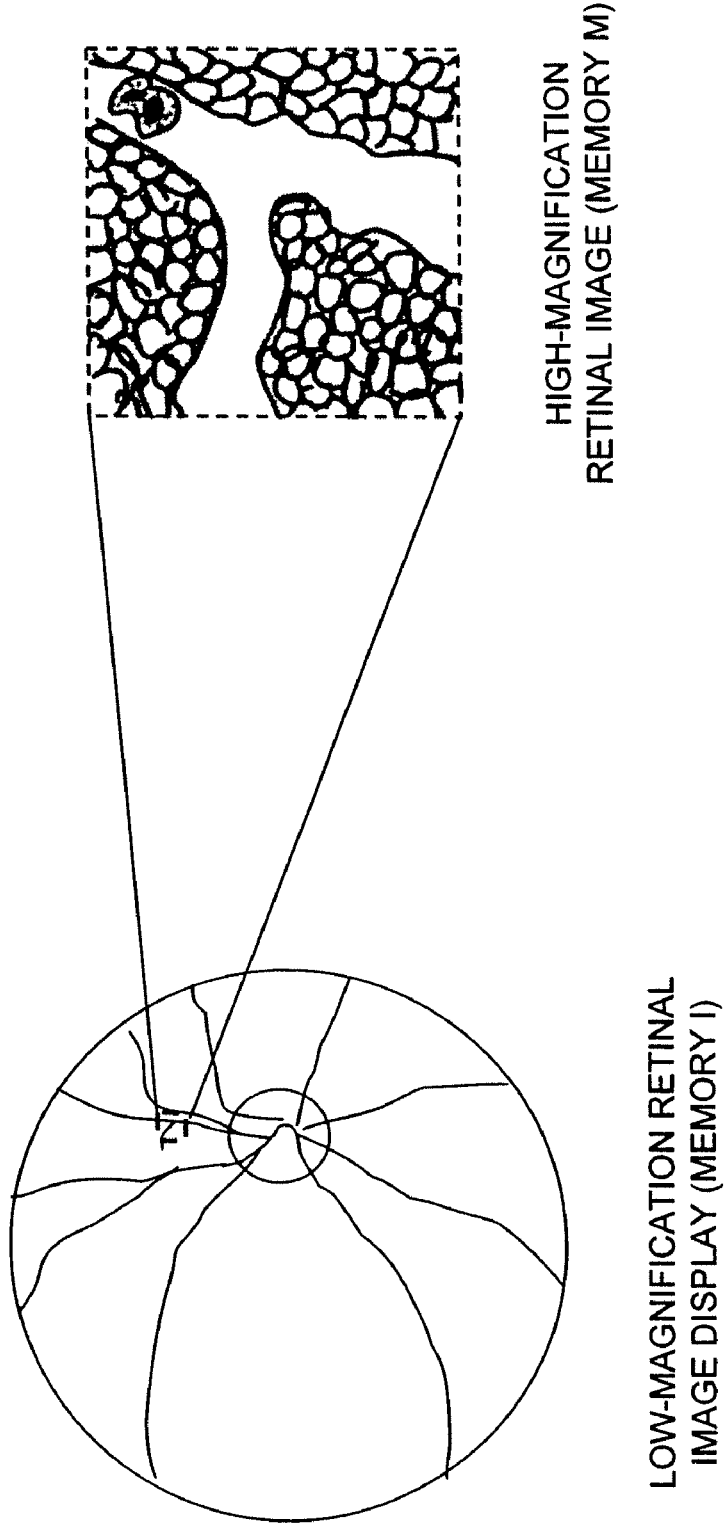
FIG. 9 is a diagram showing a display example of low-magnification and high-magnification retinal image pickup.

FIG. 9 is a diagram showing a display example of picking up the low-magnification and high-magnification retina.

With respect to the low-magnification retinal image stored in the memory I, an image of a broad range such as the overall retina can be displayed, for example. With respect to the high-magnification retinal image stored in the memory M, an image at a desired position can be displayed at a high magnification. In the case of the low-magnification retinal image, an indicated position or range may be displayed, for example.

(Blood Flow Rate Measuring Mode)

Figure 7:
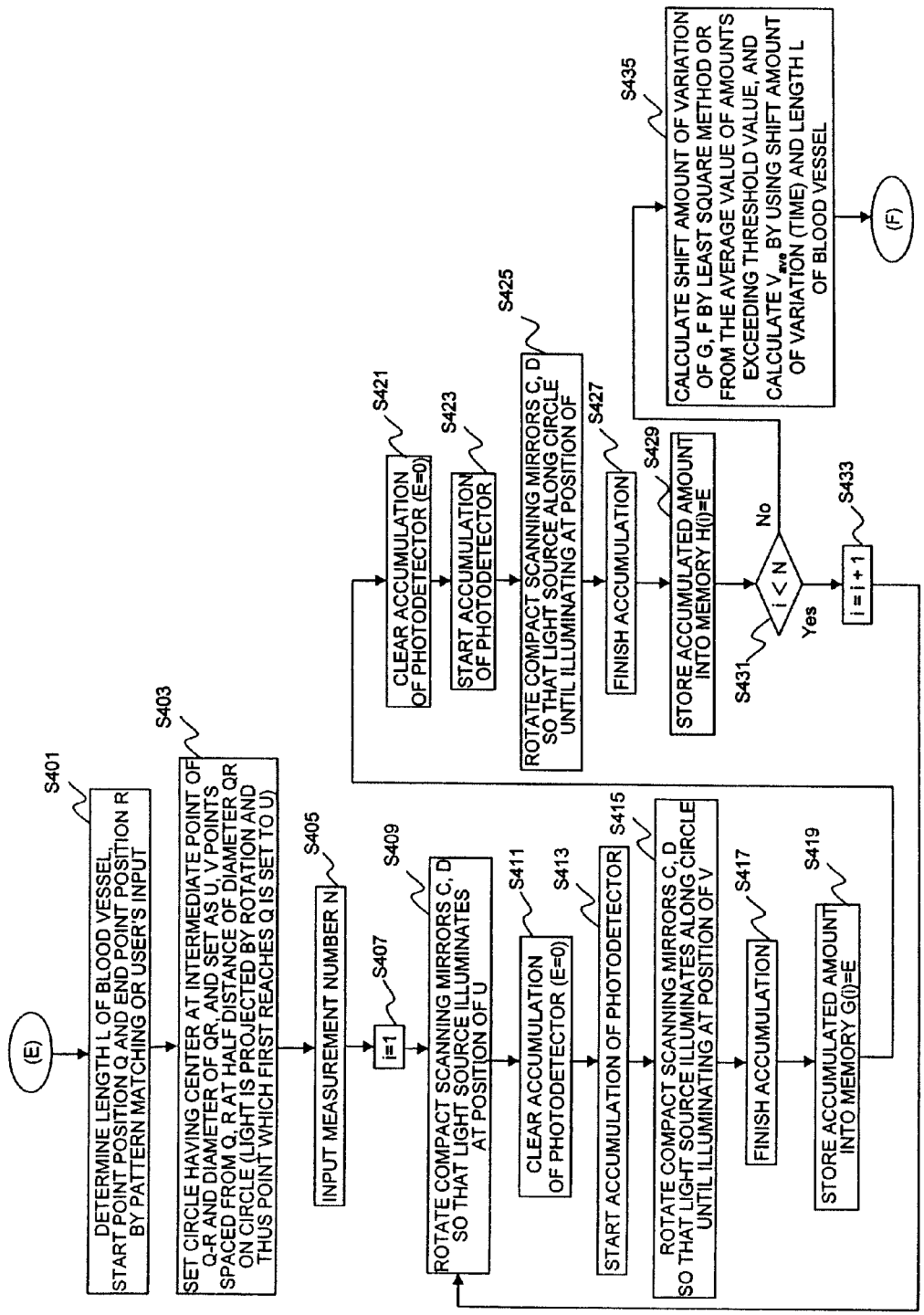
FIG. 7 is a flowchart showing calculation of blood flow rate.
Figure 8:
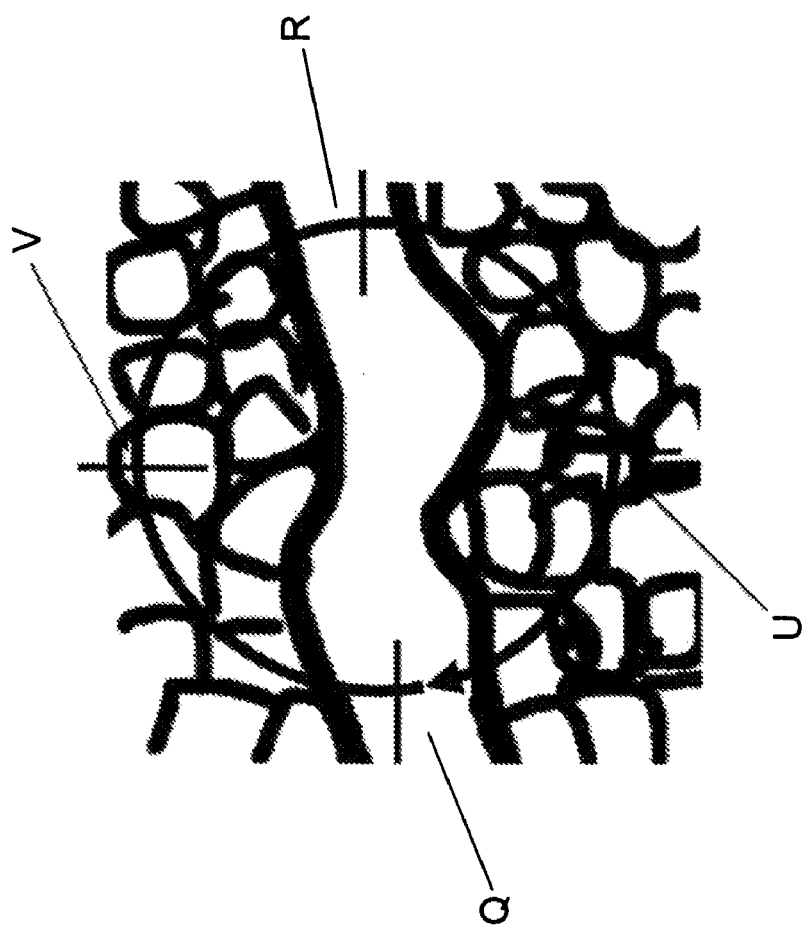
FIG. 8 is a diagram showing calculation of blood flow rate.

FIG. 7 is a flowchart showing blood flow rate calculation, and a detailed flowchart of the above step S400. Furthermore, FIG. 8 is a diagram showing the blood flow rate calculation, and FIG. 10 is a diagram showing a display example of the blood flow rate measurement and a result of the blood flow rate measuring mode.

The processor 600 sets the length L of a blood vessel under measurement, a start point position Q and an end point position R (S401). For example, the processor 600 determines the length L of the blood vessel under measurement, the start point position Q and the end point position R by pattern matching or user's input.

According to the pattern matching, for example, a blood vessel is extracted through the image processing, and the length L, the start point position Q and the end point position R are determined on the basis of the blood vessel image. A profile and a step function of a typical blood vessel are used as an original pattern, and the correlation with them may be calculated.

More specifically, the processor 600 extracts the portion corresponding to the blood vessel from the low-magnification retinal image achieved in step S200. Subsequently, the processor 600 determines the start point Q of the blood vessel. Any position may be set as the start point insofar as it is in the neighborhood of the center of the vessel on the blood vessel. For example, a position near to the center of the image or the like may be selected. Subsequently, the processor 600 determines the end point R of the blood vessel. Any position which is spaced from the start point Q by some degree and in the neighborhood of the center of the vessel on the blood vessel may be selected as the end point R as in the case of the start point. Actually, if the end point is so far from the start point, the scan speed would be insufficient and the signal intensity would be reduced. Therefore, an error would be increased if the end point is so far from the start point. Subsequently, the processor 600 connects the start point Q and the end point R by a curved line or a straight line which passes through the center of the blood vessel and calculates the length L therebetween. The length from the start point may be predetermined, and the end point may be determined on the basis of the start point and the length. In this embodiment, the start point and the end point of the blood vessel are referred to, however, they are used to define a circle for determining an orbit to be scanned, the distance of the blood vessel, etc. in the blood flow rate measurement of this embodiment, and they do not represent the actual end points of the blood vessel.

Furthermore, according to the user's input, by moving a mouse, a touch pane or the like that the movement is along the blood vessel on the image displayed on the display portion, the start point position Q, the end point position R and the length L of the blood vessel can be indicated from the start position, the moving distance and the end position. Furthermore, the blood vessel on the image has a high magnification, and thus it is substantially linear. Therefore, even a method of measuring the distance on the basis of the start position and the end position has a little error, and thus the length L of the blood vessel may be calculated from the input start point position Q and end point position R.

Subsequently, the processor 600 sets points U and V (S403). As an example, as shown in FIG. 8, a circle whose center corresponds to the intermediate point between Q and R and whose diameter corresponds to QR is provided, and points which are located on the circle and spaced from Q, R by a half of the distance QR are set as U, V. Light is projected while rotating, and thus the point which first reaches the point Q is set to U. The processor 600 carries out the measurement by rotating light on the circle having the distance between Q and R as the diameter.

The processor 600 inputs the measurement frequency N from the input section by the operation of the operator (S405). In order to set the measurement frequency N, for example, the processor 600 or the like may read out the predetermined measurement frequency N from the memory 800. An indication for promoting input of the measurement frequency N may be displayed on the display section 700. The processor 600 carries out initialization (S407). For example, the processor 600 sets the parameter i so that i=1. In this case, i represents the measurement frequency.

The processor 600 rotates the compact scanning mirrors C83 and D84 so that a light beam is at the position of U (S409). For example, the processor 600 controls the fifth driving section 914 and the sixth driving section 915 by the controller 610 to rotate the compact scanning mirror C83 and the compact scanning mirror D84 so that the light beam is at the position of U set in step S403. The processor 600 clears the light accumulation of the photodetector 32 (accumulation amount E=0) (S411). The processor 600 starts illumination from the light source 17 at a proper timing, and starts light accumulation of the photodetector 32 (S413).

The processor 600 rotates the compact scanning mirrors C83 and D84 until the light beam reaches the position of V along a circle (S415). For example, the processor 600 controls the fifth driving section 914 and the sixth driving section 915 by the controller 610 to rotate the compact scanning mirror C83 and the compact scanning mirror D84 until the light beam reaches the position of V from the position of U while the light beam moves along the circle having the diameter of QR. The processor 600 finishes the light accumulation of the photodetector 32 after the light beam is rotated from the point V to the point U in step S415 (S417).

The processor 600 stores the accumulation amount E (first light amount) into the memory 800 (S419). For example, the processor 600 stores the amount E accumulated in the photodetector 32 in association with the measurement frequency i into the memory 800 (in this case, it is assumed to be the memory G). The processor 600 clears the light accumulation amount of the photodetector 32 (E=0) (S421).

The processor 600 starts the light accumulation of the photodetector 32 (S423). Furthermore, the processor 600 rotates the compact scanning mirrors C83 and D84 so that the light beam reaches the position of U along the circle (S425). For example, as in the case of the step S415, the processor 600 controls the light beam so that the light beam moves from the point V along the circle having the diameter of QR and reaches the position of U. The processor 600 finishes the light accumulation of the photodetector 32 (S427).

The processor 600 stores the accumulated light amount E (second light amount) into the memory 800 (S429). For example, the processor 600 stores the amount E accumulated in the photodetector 32 in association with the measurement frequency i into the memory 800 (in this case, it is assumed to be the memory H). The processor 600 judges whether the parameter i is smaller than N (S431). That is, it is judged whether the measurement has been made at N times. When the parameter i is smaller than N (S431), the processor 600 increments the value of i (for example, i=i+1) (S433), and then returns to the step S409.

As described above, the processor 600 repetitively executes the steps S409 to S431. When the measurement of the predetermined measurement frequency N is finished, the processor 600 judges in step S431 that the parameter i is larger than N (S431), and shifts to step S435.

The processor 600 calculates the shift amount of the variation of G, F by a least square method or from the average amount of the shift amounts exceeding a threshold value, the blood flow rate Vave is calculated by using the shift amount of variation (time) and the length L of the blood vessel (S435), and the blood flow rate calculation processing is finished (F). The calculation of the blood flow rate will be described.

For example, the processor 600 reads out the accumulated light amount from the memory G, F and calculates the shift amount of the variation thereof by the least-square method or from the average value of amounts exceeding some threshold value. For example, FIG. 10B shows the shift amount of the variation by an arrow, and specifically, variation of the intensity when a leukocyte or the like passes through the blood vessel is measured.

Figure 10B:
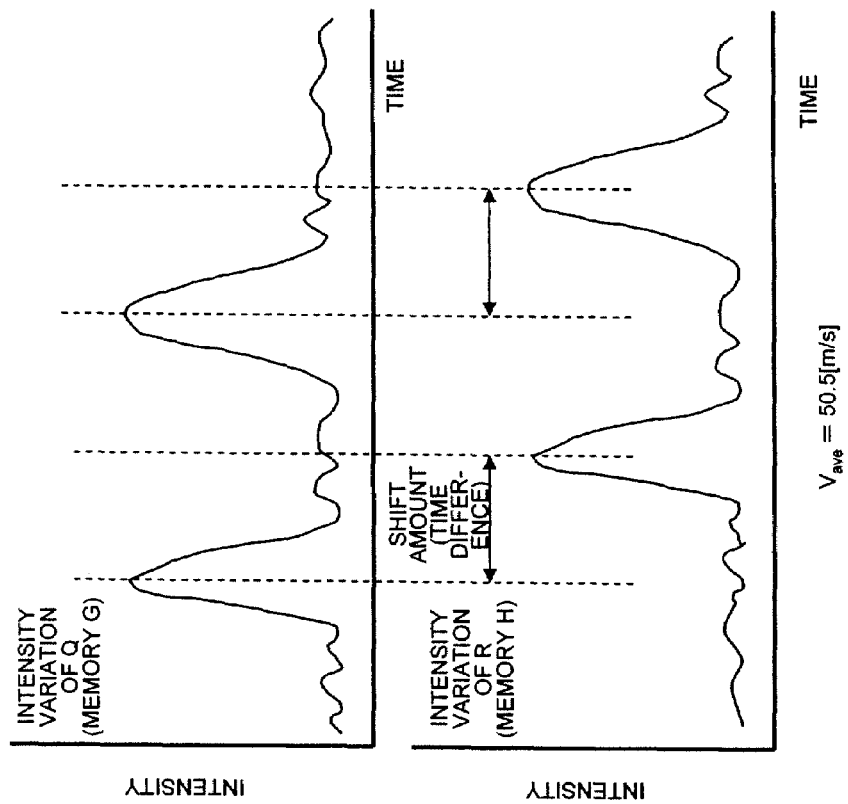
FIGS. 10A and 10B are diagrams showing a display example of blood flow rate measurement and a result of a blood flow rate measuring mode.
Figure 10A:
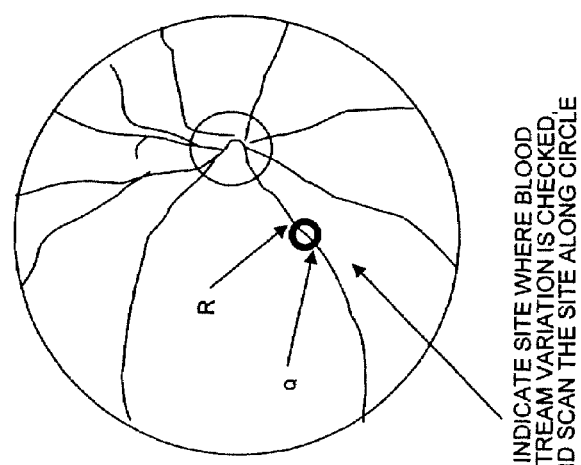

As a method of calculating the shift amount of the variation by the least square method, for example, the states that two graphs shown in FIG. 10B are most remarkably overlapped with each other when the time-axis (X-axis) is varied is determined by the least square method. For example, the state that the square of the signal difference is minimum is found by varying the X-axis. The time difference between the graph of Q and the graph of R is determined at that time. It may be normalized to some degree. In this embodiment, this time difference is called as the shift amount of variation.

As the method of calculating the shift amount of variation from the average value of amounts exceeding a threshold value, assuming that a leukocyte or the like is passing when a stored light amount exceeds a predetermined threshold value, the center of gravity of one mountain when the leukocyte or the like has passed is considered as a state that the center of the leukocyte is located at the Q, R point. The leukocyte passing over the Q point is likewise observed at the R point, and thus this is measured at several times. The time difference is measured from the average of the measurement results.

For example, the processor 600 calculates the average value of the corresponding time (first average value, the peak of the first light amount) for first light amounts exceeding a predetermined threshold value in the first light amounts stored in the memory G. Furthermore, the processor 600 calculates the average value of the corresponding time (the second average value, the peak of the second light amount) for second light amounts exceeding a predetermined threshold value in the second light amounts stored in the memory H. The processor 600 sets the difference between the calculated first average value and the calculated second average value as the shift amount of variation.

Furthermore, the processor 600 calculates the blood flow rate Vave by using the calculated shift amount (time) of variation and the length L of the blood vessel. For example, the processor 600 calculates the numerical value Vave of the blood flow rate according to the following equation.

Rate (the numerical value Vave of blood flow rate)=distance (the length L of blood vessel)/time (shift amount of variation) The processor 600 stores the calculated blood flow rate Vave into the memory 800 and/or displays it on the display section 700.

In the foregoing description, the scanning is carried out along a circular orbit. However, the scanning orbit is not limited to a circle, but it may be a proper rotational orbit such as an ellipse or the like. In the case of an ellipse, the set length L of the blood vessel may be set to a major axis or minor axis.

The present invention may be applied to a retinal image pickup device or the like, for example. Furthermore, the present invention is applicable to a device for achieving low-magnification and high-magnification images by scanning mirrors.

What is claimed is:

1. An ophthalmologic photographing apparatus, comprising:
   a light source section for emitting illumination light to illuminate a retina of an eye under measurement;
   an aberration measurement section for receiving a reflected light beam from the retina and measuring the aberrations of the eye under measurement;
   an aberration compensation section having a wavefront compensation element for compensating for the reflected light beam from the retina on the basis of the aberrations measured by the aberration measuring section so as to offset the aberrations;
   an illumination optical system that has a scanning mirror for scanning a part of the retina in a two-dimensional direction by the illumination light beam from the light source section and, illuminates the retina of the eye under measurement;
   a light-receiving optical system for receiving the reflected light beam that is illuminated through a path including the scanning mirror, reflected from the retina and compensated in aberrations by the aberration compensation section;
   a photodetector for receiving the light beam from the light-receiving optical system;
   an image forming section for forming a retinal image according to a scan position of the scanning mirror and a light-reception signal of the photodetector; and
   a calculation section for estimating a blood flow rate of a blood vessel on the retina,
   wherein
   the wavefront compensation element faces the scanning mirror, the scanning mirror and the wavefront compensation element are disposed at pupil-conjugated positions or at substantially pupil-conjugated positions,
   the scanning mirror scans the retina on a circular orbit or rotational orbit at plural times,
   the photodetector accumulates received light while one half of the circular orbit or rotational orbit is scanned, outputs an accumulated first light amount, accumulates received light while the other half of the circular orbit or rotational orbit is scanned and, outputs an accumulated second light amount, and
   the calculation section
   stores the first light amount in association with the time, stores the second light amount in association with the time,
   calculates the time difference between the peak of the first light amount and the peak of the second light amount on the basis of the time variation of the first light amount and the time variation of the second light amount, and
   divides the diameter of the circular orbit or the diameter of the rotational orbit by the calculated time difference to thereby estimate the blood flow rate,
   further wherein
   the calculation section shifts the waveform corresponding to the time variation of the first light amount and the waveform corresponding to the time variation of the second light amount in the time-axial direction to calculate a time shift amount at which both the waveforms are most remarkably overlapped with each other, and sets the time shift amount as the time difference between the peak of the first light amount and the peak of the second light amount.

2. The ophthalmologic photographing apparatus according to claim 1, wherein
   the illumination optical system further comprises a second scanning mirror that scans the retina in a broader range than the scanning mirror and is located at a pupil-conjugated position different from the positions at which the wavefront compensation element and the scanning mirror are disposed.

3. The ophthalmologic photographing apparatus according to claim 2, wherein
   the second scanning mirror scans the overall retina or a broad range of the retina with a first precision, and
   the scanning mirror scans a part of the retina or a narrow range of the retina with a second precision higher than the first precision.

4. The ophthalmologic photographing apparatus according to claim 2, wherein the image forming section achieves a first retinal image of low-magnification or broad-range by making the second scanning mirror scan while rotating the second scanning mirror, a desired position or range is indicated according to the achieved first retinal image, the second scanning mirror is fixed at a position where the neighborhood of an indicated position or range is illuminated, and the image forming section achieves a second retinal image of high-magnification in the neighborhood of the indicated position or in the indicated range by rotating the scanning mirror so that the scanning mirror scans the neighborhood of the indicated position or the indicated range.

5. The ophthalmologic photographing apparatus according to claim 4, further comprising:

a display section for displaying the achieved first retinal image, the indicated position or range according to the first retinal image, and the second retinal image at the indicated position or range.

6. The ophthalmologic photographing apparatus according to claim 2, wherein the second scanning mirror has a first mirror for scanning in an X-direction and a second mirror for scanning in a Y-direction, the first mirror is disposed at a first position conjugated with the pupil, and the second mirror is disposed at a second position that is conjugated with the pupil and is different from the first position.

7. The ophthalmologic photographing apparatus according to claim 1, wherein the scanning mirror has a first mirror for scanning in an X-direction and a second mirror for scanning in a Y-direction, the wavefront compensation element is disposed at a third position conjugated with the pupil, and the first mirror and the second mirror are disposed in the vicinity of the third position and at positions which are substantially conjugated with the pupil.

8. The ophthalmologic photographing apparatus according to claim 1, wherein the illumination optical system illuminates the retina by the illumination light beam from the light source section through an aperture diaphragm having an opening at the center portion thereof at a position conjugated with the pupil.

9. The ophthalmologic photographing apparatus according to claim 1, further comprising:

a second scanning mirror that is located at a pupil-conjugated position different from the positions in which the wavefront compensation element and the scanning mirror are disposed and is configured to scan the retina in a broader range than the range by the scanning mirror, wherein the image forming section achieves a first retinal image of low-magnification or broad-range by making the second scanning mirror scan, the calculation section displays the achieved first retinal image on the display portion, and inputs a position to be scanned that is indicated according to the displayed first retinal image, the second scanning mirror is fixed at such a position that the neighborhood of the input position is illuminated, and the scanning mirror scans the neighborhood of the input position along a circular orbit or a rotational orbit.

10. The ophthalmologic photographing apparatus according to claim 1, further comprising:

a second scanning mirror that is located at a pupil-conjugated position different from the positions at which the wavefront compensation element and the scanning mirror are disposed and is configured to scan the retina in a broader range than the range by the scanning mirror, wherein the image forming section achieves a first retinal image of low-magnification or broad-range by making the second scanning mirror scan, the calculation section indicates a matching position with a predetermined pattern image from the achieved first retinal image, the second scanning mirror is fixed at such a position that the neighborhood of the indicated position is illuminated, and the scanning mirror scans the neighborhood of the indicated position along a circular orbit or a rotational orbit.

11. An ophthalmologic photographing apparatus, comprising:

a light source section for emitting illumination light to illuminate a retina of an eye under measurement;

an aberration measurement section for receiving a reflected light beam from the retina and measuring the aberrations of the eye under measurement;

an aberration compensation section having a wavefront compensation element for compensating for the reflected light beam from the retina on the basis of the aberrations measured by the aberration measuring section so as to offset the aberrations;

an illumination optical system that has a scanning mirror for scanning a part of the retina in a two-dimensional direction by the illumination light beam from the light source section and, illuminates the retina of the eye under measurement;

a light-receiving optical system for receiving the reflected light beam that is illuminated through a path including the scanning mirror, reflected from the retina and compensated in aberrations by the aberration compensation section;

a photodetector for receiving the light beam from the light-receiving optical system;

an image forming section for forming a retinal image according to a scan position of the scanning mirror and a light-reception signal of the photodetector; and a calculation section for estimating a blood flow rate of a blood vessel on the retina, wherein the wavefront compensation element faces the scanning mirror, the scanning mirror and the wavefront compensation element are disposed at pupil-conjugated positions or at substantially pupil-conjugated positions, the scanning mirror scans the retina on a circular orbit or rotational orbit at plural times, the photodetector accumulates received light while one half of the circular orbit or rotational orbit is scanned, outputs an accumulated first light amount, accumulates received light while the other half of the circular orbit or rotational orbit is scanned and, outputs an accumulated second light amount, and the calculation section stores the first light amount in association with the time, stores the second light amount in association with the time, calculates the time difference between the peak of the first light amount and the peak of the second light amount on the basis of the time variation of the first light amount and the time variation of the second light amount, and divides the diameter of the circular orbit or the diameter of the rotational orbit by the calculated time difference to thereby estimate the blood flow rate, further wherein the calculation section calculates a first average value of the time corresponding to the first light amounts which exceeds a predetermined threshold value, calculates a second average value of the time corresponding to the second light amounts which exceeds a predetermined threshold value, and sets the difference between the first average value and the second average value as the time difference between the peak of the first light amount and the peak of the second light amount.

12. The ophthalmologic photographing apparatus according to claim 11, further comprising:

a second scanning mirror that is located at a pupil-conjugated position different from the positions at which the wavefront compensation element and the scanning mirror are disposed and is configured to scan the retina in a broader range than the range by the scanning mirror, wherein the image forming section achieves a first retinal image of low-magnification or broad-range by making the second scanning mirror scan, the calculation section indicates a matching position with a predetermined pattern image from the achieved first retinal image, the second scanning mirror is fixed at such a position that the neighborhood of the indicated position is illuminated, and the scanning mirror scans the neighborhood of the indicated position along a circular orbit or a rotational orbit.

13. The ophthalmologic photographing apparatus according to claim 11, further comprising:

a second scanning mirror that is located at a pupil-conjugated position different from the positions in which the wavefront compensation element and the scanning mirror are disposed and is configured to scan the retina in a broader range than the range by the scanning mirror, wherein the image forming section achieves a first retinal image of low-magnification or broad-range by making the second scanning mirror scan, the calculation section displays the achieved first retinal image on the display portion, and inputs a position to be scanned that is indicated according to the displayed first retinal image, the second scanning mirror is fixed at such a position that the neighborhood of the input position is illuminated, and the scanning mirror scans the neighborhood of the input position along a circular orbit or a rotational orbit.

14. The ophthalmologic photographing apparatus according to claim 11, wherein the illumination optical system further comprises a second scanning mirror that scans the retina in a broader range than the scanning mirror and is located at a pupil-conjugated position different from the positions at which the wavefront compensation element and the scanning mirror are disposed.

15. The ophthalmologic photographing apparatus according to claim 14, wherein the second scanning mirror scans the overall retina or a broad range of the retina with a first precision, and the scanning mirror scans a part of the retina or a narrow range of the retina with a second precision higher than the first precision.

16. The ophthalmologic photographing apparatus according to claim 14, wherein the image forming section achieves a first retinal image of low-magnification or broad-range by making the second scanning mirror scan while rotating the second scanning mirror, a desired position or range is indicated according to the achieved first retinal image, the second scanning mirror is fixed at a position where the neighborhood of an indicated position or range is illuminated, and the image forming section achieves a second retinal image of high-magnification in the neighborhood of the indicated position or in the indicated range by rotating the scanning mirror so that the scanning mirror scans the neighborhood of the indicated position or the indicated range.

17. The ophthalmologic photographing apparatus according to claim 16, further comprising:

a display section for displaying the achieved first retinal image, the indicated position or range according to the first retinal image, and the second retinal image at the indicated position or range.

18. The ophthalmologic photographing apparatus according to claim 14, wherein the second scanning mirror has a first mirror for scanning in an X-direction and a second mirror for scanning in a Y-direction, the first mirror is disposed at a first position conjugated with the pupil, and the second mirror is disposed at a second position that is conjugated with the pupil and is different from the first position.

19. The ophthalmologic photographing apparatus according to claim 11, wherein the scanning mirror has a first mirror for scanning in an X-direction and a second mirror for scanning in a Y-direction, the wavefront compensation element is disposed at a third position conjugated with the pupil, and the first mirror and the second mirror are disposed in the vicinity of the third position and at positions which are substantially conjugated with the pupil.

20. The ophthalmologic photographing apparatus according to claim 11, wherein the illumination optical system illuminates the retina by the illumination light beam from the light source section through an aperture diaphragm having an opening at the center portion thereof at a position conjugated with the pupil.

* * * * *